United States Patent
East

(10) Patent No.: US 6,764,468 B1
(45) Date of Patent: Jul. 20, 2004

(54) SEALED STERILE INTRAVENOUS CATHETER AND NEEDLE ASSEMBLY

(75) Inventor: Doreen May East, North Lauderdale, FL (US)

(73) Assignee: Express Exquisite, Fort Lauderdale, FL (US)

(*) Notice: Subject to any disclaimer, the term of this patent is extended or adjusted under 35 U.S.C. 154(b) by 77 days.

(21) Appl. No.: 10/271,130

(22) Filed: Oct. 15, 2002

Related U.S. Application Data (63) Continuation-in-part of application No. 09/901,228, filed on Jul. 9, 2001.

(51) Int. Cl.[7] ................................................ A61M 5/32
(52) U.S. Cl. .................. 604/192; 604/110; 604/205; 604/168.01; 604/195
(58) Field of Search ....................... 604/192, 198, 604/199, 164.01, 168.01, 110, 164.08, 164.12, 195, 263, 194, 164.02, 200, 205, 167.01

(56) References Cited

U.S. PATENT DOCUMENTS

| | | | | |
|---|---|---|---|---|
| 5,501,675 A | * | 3/1996 | Erskine | 604/263 |
| 5,823,961 A | * | 10/1998 | Fields et al. | 600/434 |
| 6,379,338 B1 | * | 4/2002 | Garvin | 604/195 |

* cited by examiner

*Primary Examiner*—Henry Bennett
*Assistant Examiner*—Camtu Nguyen
(74) *Attorney, Agent, or Firm*—Gold & Rizvi, P.A.; H. John Rizvi; Glenn E. Gold

(57) ABSTRACT

A sealed sterile intravenous catheter and needle assembly providing a substantially closed and sterile environment. The sealed sterile intravenous catheter is removably secured to a needle assembly and includes a tubular catheter portion, a catheter nozzle portion, and a gel cap portion aligned axially about a central axis to form a sealed flow passageway therethru.

The gel cap portion includes a hollow gel cap hub having a gel cap formed of an elastic material to substantially seal the gel cap portion of the sealed catheter. Additionally, the needle assembly includes a needle configured to matingly cooperate with the sealed catheter assembly and pierce through the gel cap and sealed flow passageway of the sealed catheter assembly in a fully extended position. The needle will also be structured to fully retract for safe disposal after use.

20 Claims, 7 Drawing Sheets

*Prior Art*

*Prior Art*

SEALED STERILE INTRAVENOUS CATHETER AND NEEDLE ASSEMBLY

CROSS REFERENCE TO RELATED APPLICATIONS

This application is a continuation-in-part of co-pending application Ser. No. 09/901,228, filed Jul. 9, 2001, which is incorporated by reference herein in its entirety.

BACKGROUND OF THE INVENTION

1. Field of the Invention

The present invention relates generally to intravenous catheters and needle assemblies, and more particularly, to an intravenous catheter and needle assembly configured to provide a substantially closed and sterile environment of intravenous access to the health care professional.

2. Description of the Prior Art

Intravenous needles have been in use for many years and are a necessary and indispensable part of patient healthcare in hospitals, nursing facilities, ambulances, and other environments where access into patient blood vessels or other passageways is necessary.

In the treatment of certain diseases, intravenous therapy is irreplaceable and permits medication to directly enter a patient's bloodstream for substantially faster absorption than by medications taken orally.

Unfortunately, there are a number of serious drawbacks inherent in intravenous needles making them difficult and cumbersome to use as well as a potentially dangerous vehicle for the spread of infections and disease. Initially, it is seen that intravenous needle usage typically results in localized bleeding at a patient's puncture point. The presence of blood, of course, during intravenous treatment poses an immediate threat of patient trauma and fear resulting from the sight of blood. Such trauma may, in some cases, result in a patient refusing further intravenous needle usage. Another danger posed by blood during intravenous therapy is the possible exposure to the healthcare professional to a variety of potentially lethal and contagious viruses, such as AIDS, for example, that may be carried in a patient's blood stream.

Intravenous needle assemblies generally are structured for use in an open and possibly unsterile system. In addition to putting the healthcare professional at risk, intravenous therapy typically involves exposing a patient's blood directly to the ambient air supply and greatly increases the risk of introducing a host of bacterial infections, germs, viruses, and other harmful pathogens and toxins to a patient's body.

Healthcare professionals have resorted to a variety of techniques designed to alleviate these problems. One makeshift solution is to apply localized pressure to the puncture point of a patient in an effort to control and reduce bleeding. Such an effort, although helpful, has been generally difficult and cumbersome to coordinate during intravenous therapy and depends primarily upon the skill and training of the healthcare practitioner. Other solutions have involved securing a gel cap or other sealing device to an intravenous catheter after insertion into a patient. Not only does use of a separate gel cap or sealing device add significant cost to a needle assembly, but such practices, unfortunately, still require a healthcare professional to temporarily apply localized pressure near a puncture point until the sealing device can be properly secured. Again, the success of these measures have been quite limited and depend primarily upon the care, attention, and training of the healthcare professional. Even where properly utilized, however, a patient is left exposed during the time interval that exists between initial needle insertion and proper sealing. Furthermore, securing a gel cap or other sealing device after insertion of an intravenous needle is an awkward, cumbersome, and time-consuming process and typically requires a two-handed approach demanding quick maneuvering and coordinated dexterity on the part of the healthcare professional.

Accordingly, there is an established need for a sealed sterile intravenous catheter and needle assembly that overcomes the aforementioned problems and deficiencies and provides a substantially closed and sterile environment for intravenous access to a patient.

SUMMARY OF THE INVENTION

The present invention is directed to a sealed sterile intravenous catheter and needle assembly providing a substantially closed and sterile environment for intravenous access to a patient.

An object of the present invention is to provide a sealed sterile intravenous catheter and needle assembly configured to substantially reduce the bleeding typically associated with intravenous needle use.

A further object of the present invention is to provide a sealed sterile intravenous catheter and needle assembly that reduces the risk of patient infection by minimizing exposure to the external environment.

Another object of the present invention is to provide a sealed sterile intravenous catheter and needle assembly that substantially reduces the risk of exposing healthcare workers to potential infections arising from contact with patient blood.

An additional object of the present invention is to provide a sealed sterile intravenous catheter and needle assembly that permits insertion of the needle assembly in a closed sterile system.

A further object of the present invention is to provide a sealed sterile intravenous catheter and needle assembly that can easily be made compatible for use with needle-less syringes.

Yet another object of the present invention is to provide a sealed sterile intravenous catheter and needle assembly which eliminates the need for a healthcare professional to perform the additional step of securing a gel cap assembly in place after insertion of a catheter assembly.

It is also an object of the present invention is to provide a sealed sterile intravenous catheter and needle assembly designed to substantially reduce patient anxiety and trauma resulting from the sight of a blood leak resulting from intravenous needle use.

Another object of the present invention is to provide a sealed sterile intravenous catheter and needle assembly that substantially streamlines the process of intravenous catheter and needle usage and assembly.

A further object of the present invention is to provide a sealed sterile intravenous catheter and needle assembly that eliminates the need for a healthcare professional to apply constant and continual pressure to a patient's body near the puncture point of an intravenous catheter and needle assembly.

Another object of the present invention is to provide a sealed sterile intravenous catheter and needle assembly wherein the sealed catheter assembly and gel cap portion are configured as a cost-effective one-piece unitary body rather than as a number of separately available components.

It is also an object of the present invention to provide a sealed sterile intravenous catheter and needle assembly configured as an easily assembled saline lock as desired.

In accordance with a first aspect of the invention, a sealed sterile intravenous catheter and needle assembly having a substantially closed and sterile environment is provided. The sealed sterile intravenous catheter is removably secured to a needle assembly and includes a tubular catheter portion, a catheter nozzle portion, and a gel cap portion aligned axially about a central axis to form a sealed flow passageway therethru. The gel cap portion also includes a hollow gel cap hub having a gel cap formed of an elastic material to substantially seal the gel cap portion of the sealed catheter. Additionally, the needle assembly includes a needle configured to matingly cooperate with the sealed catheter assembly and pierce through the gel cap and sealed flow passageway of the sealed catheter assembly in a fully extended position. The needle will also be structured to fully retract for safe disposal after use.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Shown throughout the figures, the present invention is generally directed towards a sealed sterile intravenous catheter and needle assembly configured to provide a substantially closed and sterile environment for intravenous access to the health care professional.

In order to appreciate the advantages and unique features of the present invention, it is necessary to first understand the shortcomings of the prior art. As such, use of a typical prior art catheter and needle assembly will be described herein in connection with prior art FIGS. 1–12.

Figure 1:
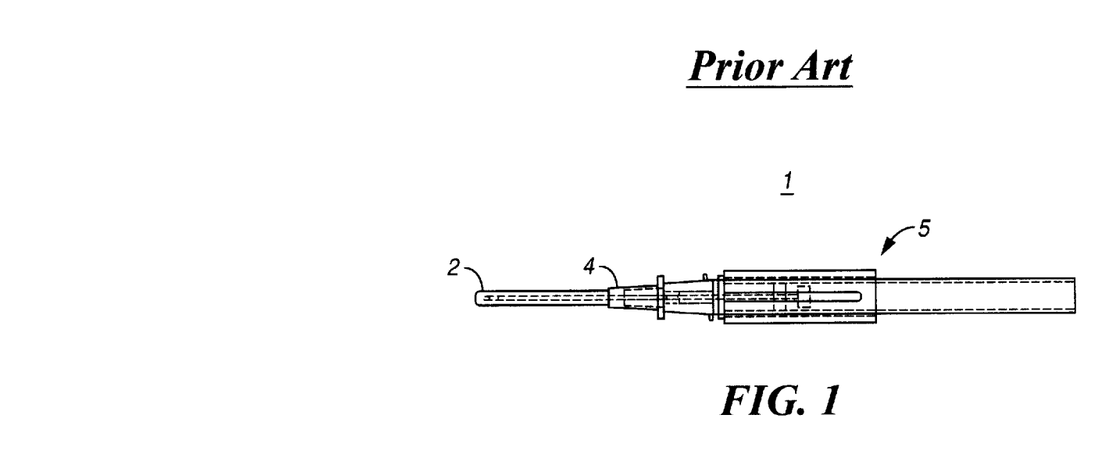
FIG. 1 is a side view showing a typical prior art catheter and needle assembly in a fully assembled configuration.
Figure 2:
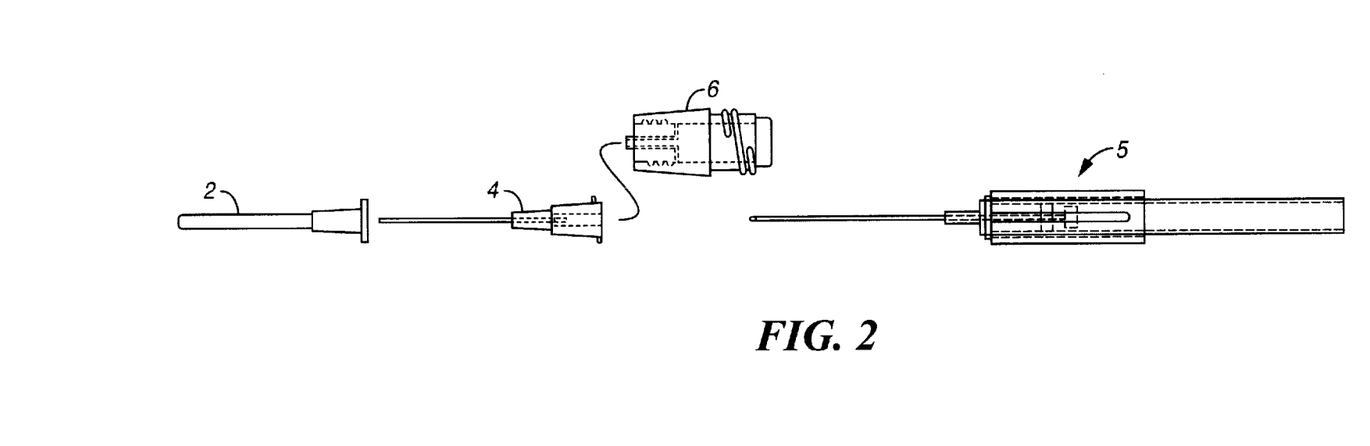
FIG. 2 is a side view showing a typical prior art catheter and needle assembly with the cap and catheter removed for positioning of a gel cap assembly.

A typical prior art catheter and needle assembly 1 is shown in a fully assembled configuration in FIG. 1. As shown in FIGS. 1–2, a typical prior art catheter and needle assembly 1 includes a cap 2, catheter assembly 4, needle assembly 5, and a gel cap assembly 6. In FIG. 2, the cap 2 and catheter assembly 4 are shown removed for positioning of the gel cap assembly 6.

Figures 3, 4:
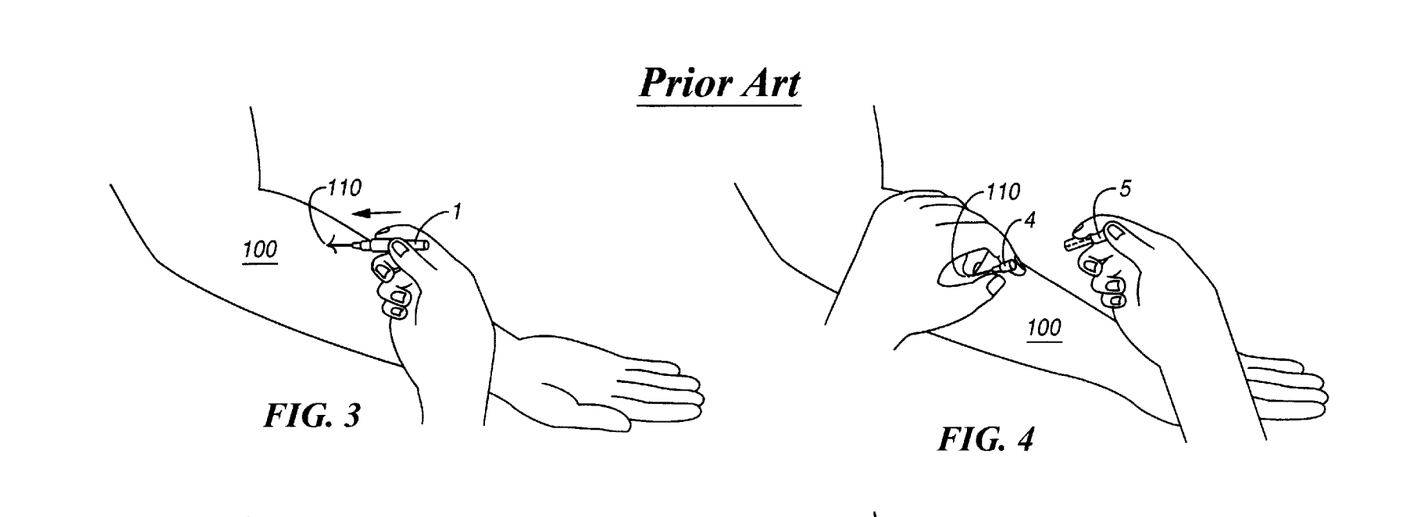
FIG. 3 is a perspective view showing a typical prior art catheter and needle assembly insertion in a patient's body.
FIG. 4 is a perspective view of a typical prior art catheter and needle assembly showing a catheter assembly left within a patient's body after removal of the needle assembly.
Figure 5:
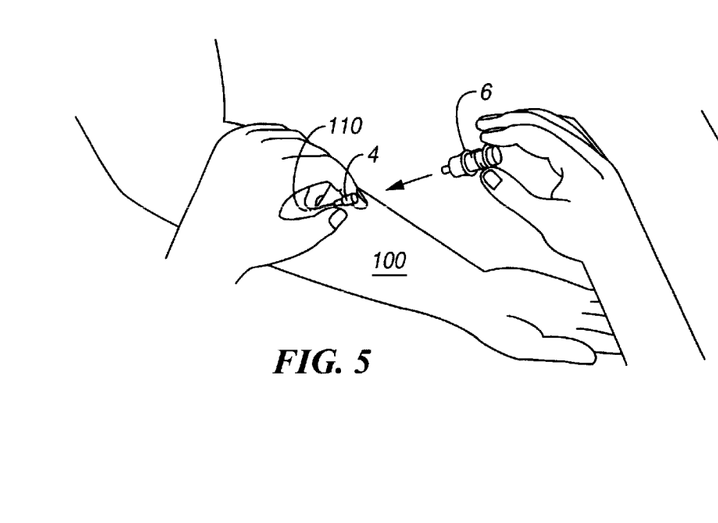
FIG. 5 is a perspective view showing a gel cap assembly being secured onto the catheter assembly of a typical prior art catheter and needle assembly while the catheter assembly is positioned in a patient's body.
Figure 6:
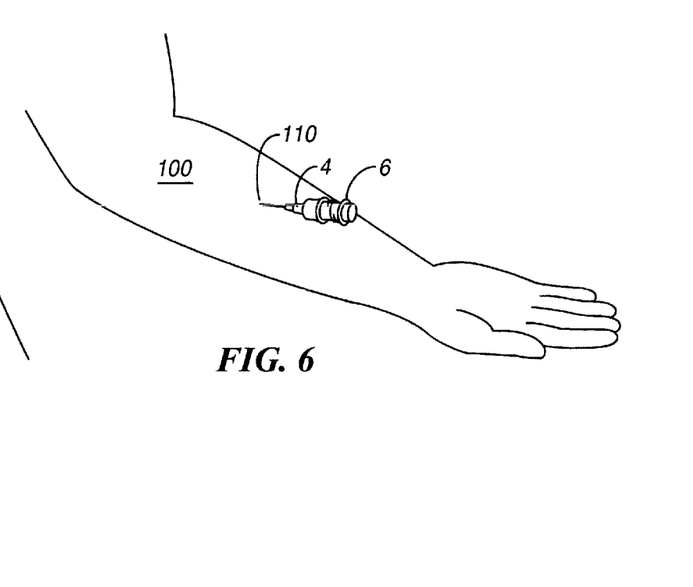
FIG. 6 is perspective view showing a typical prior art catheter assembly and gel cap assembly positioned in a patient's body.

The prior art catheter and needle assembly 1 is shown just prior to insertion into a patient's body 100 in FIG. 3. Although any of a wide variety of different locations on a patient's body are suitable for intravenous needle insertion, the figures referred to herein will consistently feature a patient's arm for simplicity. Referring now to FIG. 4, the needle assembly 6 is removed leaving the catheter assembly behind in a patient's body 100. It should be noted, however, that while one end of the catheter assembly 4 is lodged within the patient's body, the other end is left exposed to atmospheric conditions. It is seen that a direct open passageway exists potentially exposing the patient to a host of bacterial infections, germs, viruses, and other harmful pathogens and toxins. Additionally, significant bleeding can occur during traditional intravenous needle insertion and it is necessary that a healthcare professional apply continuous and constant pressure near the puncture point 110 to prevent blood from leaking through and exiting through the catheter assembly. With existing catheter and needle assemblies, a healthcare professional must apply continuous pressure near the puncture point 110 while simultaneously reaching for a gel cap assembly 6 to secure into place on the catheter assembly 4 as shown in FIG. 5. The gel cap assembly 60 of the prior art prevents blood from leaking out of the catheter assembly 4 and provides a saline lock as desired. In FIG. 6, the catheter assembly 4 and gel cap assembly 6 are shown left in a patient's body 100.

Figure 7:
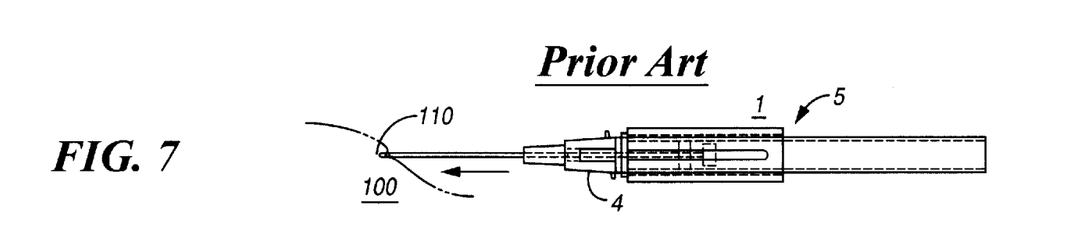
FIG. 7 is a side view showing a typical prior art catheter and needle assembly before insertion into a patient's body.
Figure 8:
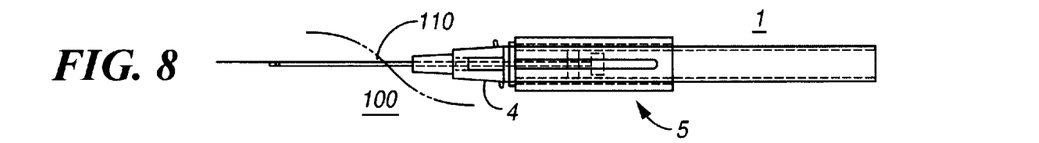
FIG. 8 is a side view showing a typical prior art catheter and needle assembly after initial insertion into a patient's body.
Figure 9:
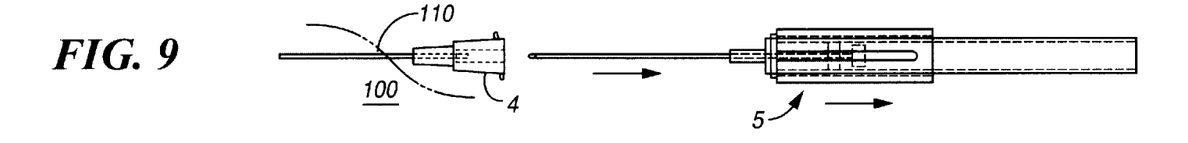
FIG. 9 is a side view showing a typical prior art catheter and needle assembly after removal of the needle assembly showing the needle in an extended position.
Figure 10:
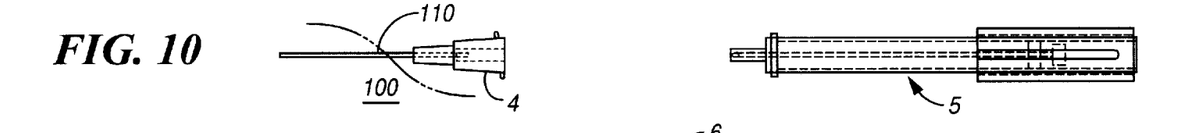
FIG. 10 is a side view showing a typical prior art catheter and needle assembly after removal of the needle assembly showing the needle in a fully retracted position.

A side view of a typical prior art catheter and gel cap assembly 1 is shown in FIG. 7 with the cap 2 removed before insertion into a patient's body 100. FIG. 8 shows the prior art catheter and needle assembly 1 after insertion. As shown in FIG. 8, At this point, the needle assembly 5 may be retracted and removed as shown in FIGS. 9–10. FIG. 9 shows the needle assembly 5 in an extended position for clarity purposes. In practice, however, the needle is typically retracted before complete withdrawal due to safety concerns. In FIG. 10, the prior art needle assembly 5 is completely withdrawn from a patient's body and shown in a fully retracted position.

Figure 11:
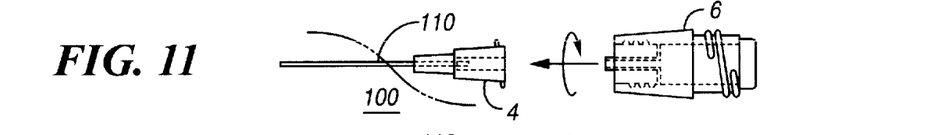
FIG. 11 is a side view showing a typical prior art catheter assembly positioned in a patient's body and a gel cap assembly before securement.
Figure 12:
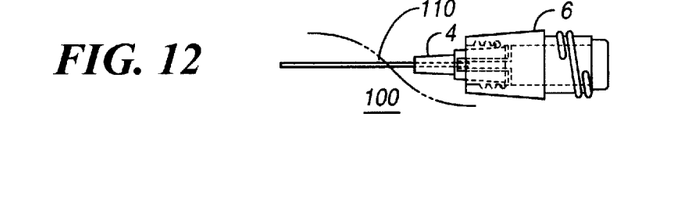
FIG. 12 is a side view showing a typical prior art catheter assembly positioned in a patient's body with a gel cap assembly fully secured in place.

After removal of the prior art needle assembly 5, it is necessary to secure a gel cap assembly 6 in place as depicted in FIG. 11. FIG. 12 shows the prior art catheter assembly 4 with a gel cap assembly 6 secured in place and inserted in a patient's body 100.

Now that the methods and apparatus utilized in the prior art have been described in relation to FIGS. 1–12, the advantages and novel features of the present invention will be better understood. Referring now to FIGS. 13–23, the sealed sterile intravenous catheter and needle assembly 10 of the present invention will be described in detail.

Figure 13:
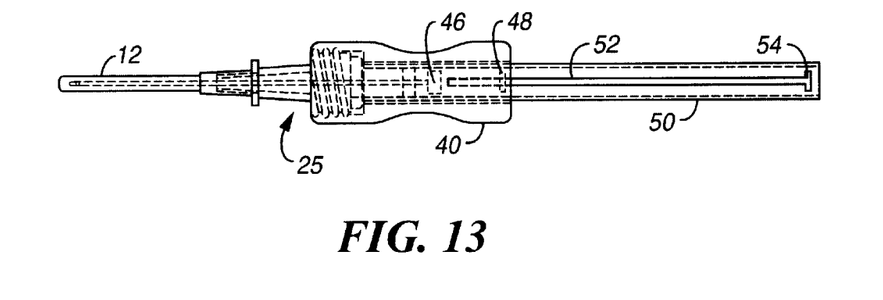
FIG. 13 is a side view showing the sealed sterile intravenous catheter and needle assembly of the present invention in its fully assembled configuration.

The sealed sterile invervenous catheter and needle assembly 10 of the present invention is shown fully assembled in FIG. 13. The cap 12 and sealed catheter assembly 20 are easily removed and shown separated from the needle assembly 60 in FIG. 14. In the preferred embodiment, the sealed catheter assembly 20 is configured to be removably secured to the needle assembly 60 as will become clear later. Similarly, as shown, the cap 12 will also be configured to cover portions of the sealed catheter assembly 20 and needle assembly 60 when in a fully assembled configuration.

Figure 14:
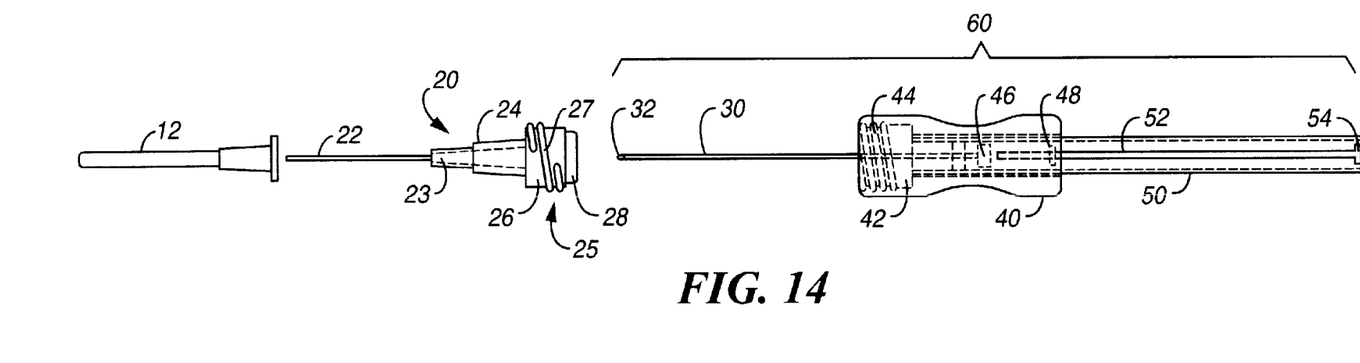
FIG. 14 is a side view showing the sealed sterile intravenous catheter and needle assembly of the present invention with the cap and sealed catheter assembly separated from the needle assembly.

The sealed catheter assembly 20 of the present invention includes a tubular catheter portion 22 as shown in FIG. 14. The tubular catheter portion 22 may be formed of any of a wide variety of materials and configurations without departing from the present invention. In the preferred embodiment, the tubular catheter portion 22 will be formed of a substantially flexible material to allow it to bend and yield where necessary. The tubular catheter portion 22 will be formed in a generally hollow configuration to permit entry of needle 30 therein as will become clear later.

The sealed catheter assembly 20 of the present invention will preferably include a catheter nozzle portion 24 as illustrated in FIG. 14. The catheter nozzle portion 24 will preferably be formed to align axially with a central axis of the tubular catheter portion 22 of the sealed catheter assembly 20 to form a sealed flow passageway 23 therethru. Although a wide variety of materials can be utilized to form the catheter nozzle portion 24, in the preferred embodiment, it will be formed of a rigid plastic material. In the preferred embodiment, the catheter nozzle portion 24 will be formed in a generally conical configuration as shown and will become narrower towards the end meeting the tubular catheter portion 22 as shown. The generally conical configuration of the catheter nozzle portion 24 will assist in directing a needle 30 towards the tubular catheter portion 22.

The sealed catheter assembly 20 of the present invention will include a gel cap portion 25 as shown in FIG. 14. The gel cap portion 25 will be configured to substantially seal the sealed catheter assembly 20 and prevent entry of a host of bacterial infections, germs, viruses, and other harmful pathogens and toxins through the sealed catheter assembly 20. As such, it will be appreciated by those skilled in the art that the sealed catheter assembly 20 of the present invention will substantially reduce exposure of a patient to the external air so as to provide a sterile environment for intravenous catheter insertion and provide a suitable saline lock during intravenous therapy as desired. The gel cap portion 25 of the present invention includes primarily a gel cap hub 26 and a gel cap 28 as shown in FIG. 14. The gel cap hub 26 will preferably be hollow and configured to be aligned axially with the sealed flow passageway 23 of the sealed catheter assembly 20 to permit the needle 30 of the needle assembly 60 to extend through the gel cap hub 26 and into the sealed flow passageway 23 in a fully extended position as will become clear later. In the preferred embodiment, securement means will be provided to removably secure said sealed catheter assembly 20 to said needle assembly. Any of a wide variety of securement means may be utilized for this purpose without departing from the present invention. In a most preferred embodiment, the securement means will comprise threads 27 on the gel cap hub 26 configured to engage cooperating threads 44 on the needle assembly 60.

The gel cap 28 of the gel cap portion 25 of the sealed catheter assembly 20 may be formed of any of a wide variety of materials. In the preferred embodiment, the gel cap will be formed of an elastic material configured to matingly correspond with the gel cap hub 26 so as to substantially seal the gel cap portion 25 of the sealed catheter assembly 20.

The sealed sterile intravenous catheter and needle assembly 10 of the present invention includes a needle assembly 60 as shown in the figures. The needle assembly 60 will preferably include retracting means so that the needle 30 can be fully retracted after use for safe disposal as will be described in more detail herein.

It will be appreciated by those skilled in the art that any of a wide variety of different configuration may be utilized for the needle assembly 60 of the present invention. In a most preferred embodiment, the needle assembly 60 will comprise an outer barrel 40 slidably mounted on an inner barrel 50 and securing a needle 30 therein as shown in FIG. 14. The needle 30 may be any of a wide variety of known needles having a generally hollow interior 32. In the preferred embodiment, the outer barrel 40 of the needle assembly 60 will be slidably mounted on the inner barrel 50, as shown, such that movement of the outer barrel 40 relative to the inner barrel 50 will retract the needle 30 within said inner barrel 50 for safe disposal. Any of a variety of different retracting means may be utilized to permit needle 30 to fully retract after use for safe disposal. In the most preferred embodiment, the retracting means will include providing the inner barrel 50 with a retraction slot 52 therein such that outer barrel 40 slides within said retracting slot 52 and into a retracted position as desired.

In the preferred embodiment, the sealed sterile intravenous catheter and needle assembly 10 of the present invention will be configured such that the needle 30 locks into a retracted position after use to prevent accidental pricks and injuries. This can be accomplished by utilizing any of a wide variety of different structural configurations without departing from the present invention. In a most preferred embodiment, the inner barrel 50 of the needle assembly 60 will include a locking slot 54 therein as shown in the figures. A corresponding locking tab 48 will be included on the outer barrel 40 and configured to slide into place in the locking slot 54 of the inner barrel 50 as the needle assembly 60 is moved to a fully retracted orientation as best illustrated in FIG. 21.

Figure 15:
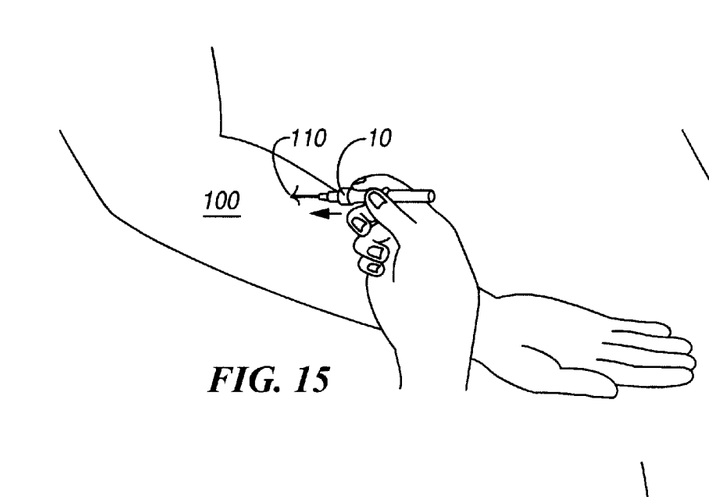
FIG. 15 is a perspective view showing the sealed sterile intravenous catheter and needle assembly of the present invention inserted into a patient's body.
Figure 16:
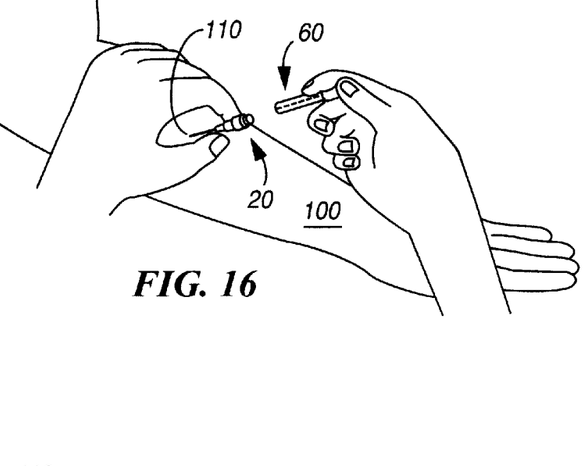
FIG. 16 is a perspective view showing the needle assembly of the present invention being removed from the sealed catheter assembly.
Figure 17:
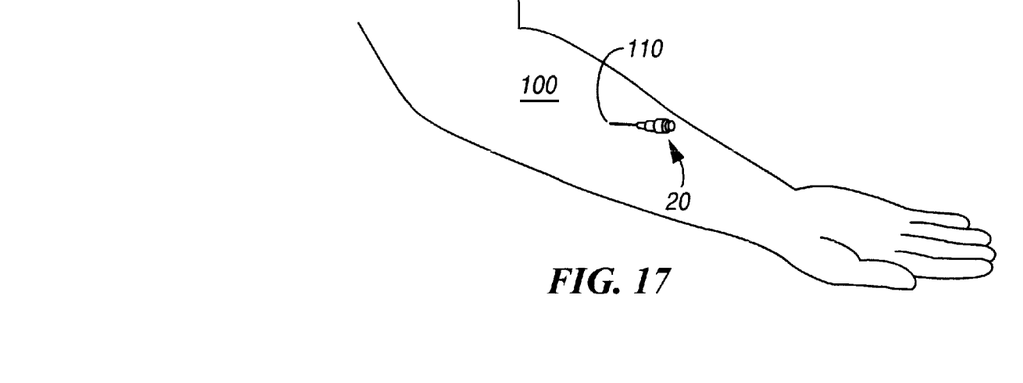
FIG. 17 is a perspective view showing the sealed catheter assembly of the present invention left within a patient's body after removal of the needle assembly.
Figure 18:
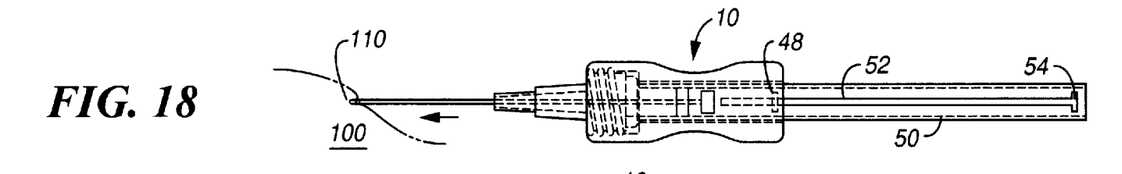
FIG. 18 is a side view showing the sealed sterile intravenous catheter and needle assembly of the present invention prior to insertion into a patient's body.

The intravenous catheter and needle assembly 10 of the present invention is shown just prior to insertion into a patient's body 100 in FIG. 15. Once the needle 30 extends through the sealed catheter assembly 20 and into the patient's body 100, as shown generally in FIG. 16, the needle 30 may be retracted and the needle assembly 60 discarded. The sealed catheter assembly 20 may remain embedded in the patient's body 100 as illustrated in FIG. 17.

Figures 19, 20:
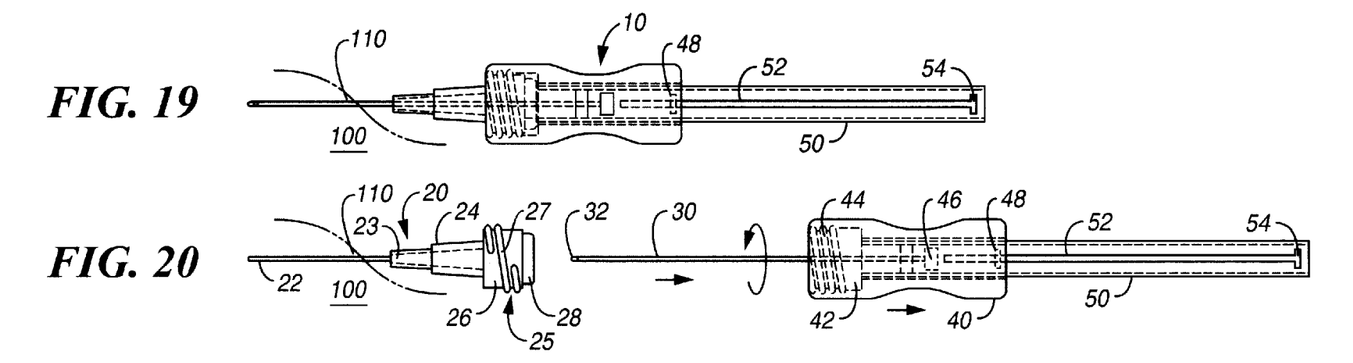
FIG. 19 is a side view showing the sealed sterile intravenous catheter and needle assembly of the present invention after initial insertion into a patient's body.
FIG. 20 is a side view showing the sealed sterile intravenous catheter and needle assembly of the present invention after removal of the needle assembly showing the needle in a fully extended position.
Figure 21:
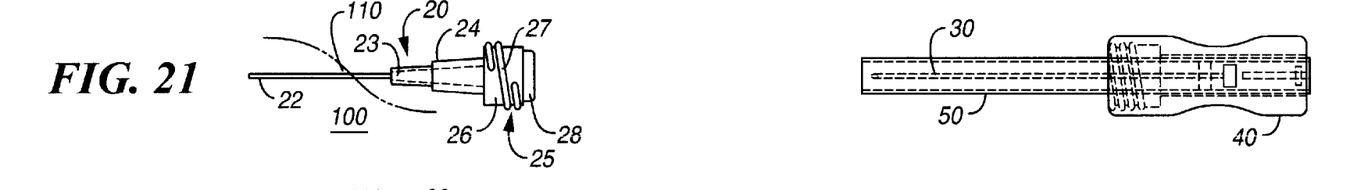
FIG. 21 is a side view showing the sealed sterile intravenous catheter and needle assembly of the present invention after removal of the needle assembly showing the needle in a fully retracted position.
Figure 22:
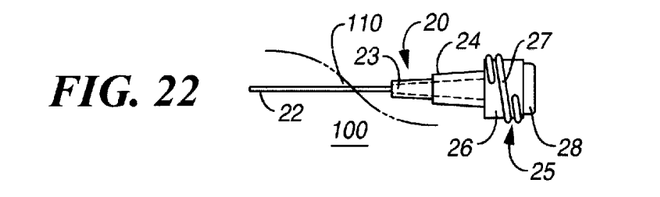
FIG. 22 is a side view showing the sealed sterile intravenous catheter and needle assembly of the present invention after removal of the needle assembly showing the needle in a fully extended position.

Detailed views illustrating different configurations during insertion of the sealed sterile intravenous catheter and needle assembly 10 of the present invention are provided in FIGS. 18–22 and described herein. A side view of the sealed sterile intravenous catheter and needle assembly 10 of the present invention is provided in FIG. 18 before insertion into a patient's body 100. FIG. 19 shows the sealed sterile intravenous catheter and needle assembly 10 after insertion. Upon insertion into the patient's body 100, a flash of blood will be viewable through the view cavity 46 as it exits the distal end of the needle 30. At this point the needle assembly 60 may be retracted and removed as shown in FIGS. 20–21. FIG. 20 shows the needle assembly in an extended position for clarity purposes. In practice, however, it is recommended that the needle 30 be completely retracted before withdrawal from a patient's body 100 to prevent accidental injuries resulting from the needle 30. In FIG. 21, the sealed sterile intravenous catheter and needle assembly 10 is completely withdrawn from a patient's body and shown in a fully retracted position. As shown in FIG. 22, the sealed catheter assembly 10 is left intact in the patient's body 100. As previously described, the gel cap portion 25 is sealed with a gel cap 28 within the gel cap hub 26, thus maintaining the sealed flow passageway 23 of the sealed catheter assembly 20 in a sealed and sterile condition. Additionally, it is seen that the gel cap portion 25 helps prevent blood from leaking from the sealed catheter assembly 20.

It will be appreciated by those skilled in the art that the needle assembly described herein and shown in the accompanying figures is provided as an illustrative embodiment only and not in a limiting sense. Turning now to the figures, it is seen that needle 30 is shown secured to the outer barrel 40 and slides along with the outer barrel 40 as desired. It should be clear to those skilled in the art that the needle 30 may, alternatively, be secured to the inner barrel of 50 of the needle assembly 60 to permit it to move in conjunction with the inner barrel 50 if desired. This embodiment provides the advantage of permitting the needle 30 depth to be easily adjustable as the sealed catheter assembly 20 is inserted into a patient's body 100. Another advantage of this configuration is that the needle 30 can easily be fully retracted before any removal of the needle assembly 60 from the sealed catheter assembly 20 is even initiated. Of course, this embodiment is only presented as an additional illustrative example and it will be clear to those skilled in the art that any of a myriad of other configurations may also be utilized for the needle assembly 60 without departing from the present invention.

Figure 23:
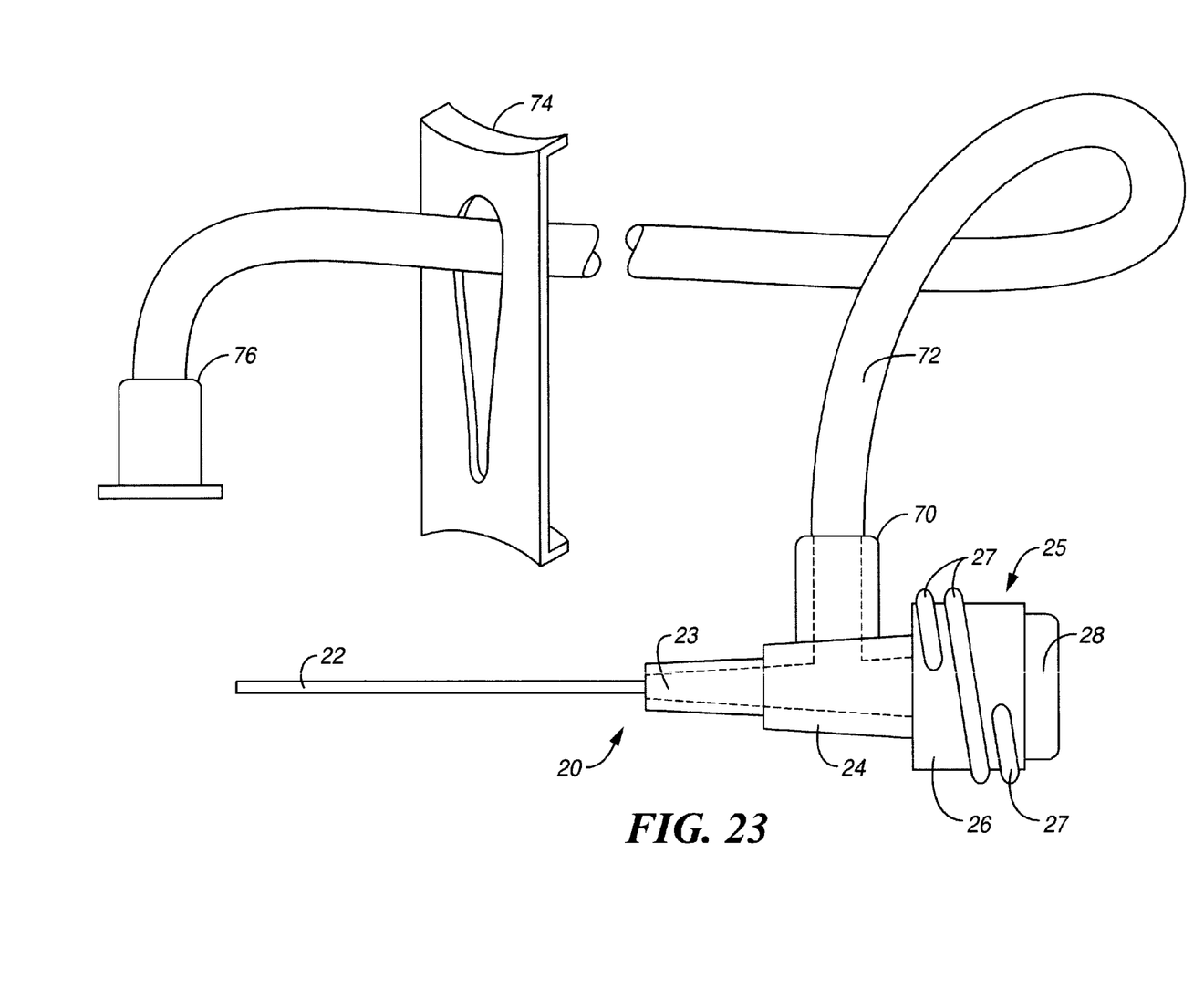
FIG. 23 is a perspective view showing an alternative embodiment of the sealed catheter assembly of the present invention shown configured for a needle-less connection.

In another alternative embodiment, the sealed catheter assembly 20 of the present invention may be provided with additional tubing connector 70 from which tube 72 extends to permit a needle-less connection at a distal connector end 76 thereof. It should be appreciated that the connecter end 76 shown in FIG. 23 is meant to be illustrative in nature only and any of a wide variety of known distal connector ends 76 may be utilized without departing from the present invention. If desired, a flow stop 74 may be provided, as shown in FIG. 23, to assist in regulating fluid flow through the tube 72 extending from the additional tubing connector 70.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A sealed sterile intravenous catheter and needle assembly comprising:

a sealed catheter assembly removably secured and configured for cooperative engagement with a needle assembly, securement means configured to removably secure said sealed catheter assembly to said needle assembly, said sealed catheter assembly formed in a generally elongate tubular configuration with a hollow flow passageway extending at least partially therethru, and said sealed catheter assembly including a gel cap portion configured to substantially seal a distal end of said sealed catheter assembly while permitting a needle of said needle assembly to pierce through a generally central axis of said gel cap portion and into said hollow flow passageway of said sealed catheter assembly.

2. A sealed intravenous catheter and needle assembly as recited in claim 1, wherein said sealed catheter assembly further comprises a tubular catheter portion and catheter nozzle portion aligned axially about a central axis to form a sealed flow passageway therethru.

3. A sealed sterile intravenous catheter and needle assembly as recited in claim 1, wherein said gel cap portion includes a generally hollow gel cap hub and a gel cap.

4. A sealed sterile intravenous catheter and needle assembly as recited in claim 3, wherein said gel cap is formed of an elastic material configured to matingly correspond to said gel cap hub and substantially seal said gel cap portion of said sealed catheter.

5. A sealed sterile intravenous catheter and needle assembly as recited in claim 1, wherein said needle of said needle assembly is configured to matingly cooperate with said sealed catheter assembly such that said needle will pierce through said gel cap portion and into said sealed flow passageway of said sealed catheter assembly in a fully extended position.

6. A sealed sterile intravenous catheter and needle assembly as recited in claim 1, wherein said needle assembly further comprises:

an elongate outer barrel securing said needle therein, said outer barrel slidably mounted on an inner barel such that movement of said outer barrel relative to said inner barrel will retract said needle within said inner barrel for safe disposal.

7. A sealed sterile intravenous catheter and needle assembly as recited in claim 6, wherein said needle assembly further comprises locking means configured to lock said needle in a fully retracted position for safe disposal.

8. A sealed sterile intravenous catheter and needle assembly as recited in claim 7, wherein said locking means comprise a locking slot disposed on said inner barrel configured to cooperatively mate with a locking tab on said outer barrel to engage said needle in a fully retracted position for safe disposal.

9. A sealed sterile intravenous catheter and needle assembly as recited in claim 1 wherein said securement means includes threads disposed on said sealed catheter assembly configured to removably engage cooperating threads on said needle assembly.

10. A sealed sterile intravenous catheter and needle assembly as recited in claim 1, wherein said sealed catheter assembly and said gel cap portion are configured as a one-piece unitary body.

11. A sealed sterile intravenous catheter and needle assembly as recited in claim 2, wherein an interior of said catheter nozzle portion is structured in a generally conical configuration and widens gradually in a direction extending axially away from said tubular catheter portion.

12. A sealed sterile intravenous catheter and needle assembly comprising:
 a sealed catheter assembly removably secured and configured for cooperative engagement with a needle assembly,
 securement means configured to removably secure said sealed catheter assembly to said needle assembly,
 said sealed catheter assembly comprising a tubular catheter portion, catheter nozzle portion, and a gel cap portion aligned axially about a central axis to form a sealed flow passageway therethru,
 said gel cap portion including a generally hollow gel cap hub and a gel cap,
 said gel cap formed of an elastic material configured to matingly correspond to said gel cap hub and substantially seal said gel cap portion of said sealed catheter assembly,
 said needle assembly including a needle configured to matingly cooperate with said sealed catheter assembly such that said needle will pierce through said gel cap and into said sealed flow passageway of said sealed catheter assembly in a fully extended position, and
 retracting means configured to retract said needle from said sealed flow passageway into a fully retracted position for safe disposal after use.

13. A sealed sterile intravenous catheter and needle assembly as recited in claim 12, wherein said needle assembly further comprises:
 an elongate outer barrel securing said needle therein, said outer barrel slidably mounted on an inner barrel such that movement of said outer barrel relative to said inner barrel will retract said needle within said inner barrel for safe disposal.

14. A sealed sterile intravenous catheter and needle assembly as recited in claim 12, wherein said gel cap hub of said sealed catheter assembly includes threads thereupon structured to engage cooperating threads on said needle assembly.

15. A sealed sterile intravenous catheter and needle assembly as recited in claim 13, wherein said needle assembly further comprises locking means configured to lock said needle in a fully retracted position for safe disposal.

16. A sealed sterile intravenous catheter and needle assembly as recited in claim 15, wherein said locking means comprise a locking slot disposed on said inner barrel configured to cooperatively mate with a locking tab on said outer barrel to engage said needle in a fully retracted position for safe disposal.

17. A sealed sterile intravenous catheter and needle assembly comprising:
 a sealed catheter assembly removably secured and configured for cooperative engagement with a needle assembly,
 said sealed catheter assembly comprising a tubular catheter portion, catheter nozzle portion, and a gel cap portion aligned axially about a central axis to form a sealed flow passageway therethru,
 said gel cap portion including a generally hollow gel cap hub and a gel cap,
 said gel cap formed of an elastic material configured to matingly correspond to said gel cap hub and substantially seal said gel cap portion of said sealed catheter, and
 said needle assembly comprises an elongate outer barrel having a needle secured therein and an elongate inner barrel, said outer barrel configured to slide relative to said inner barrel so that said needle retracts within said inner barrel for safe disposal.

18. A sealed sterile intravenous catheter and needle assembly as recited in claim 17, wherein an interior of said catheter nozzle portion is structured in a generally conical configuration and widens gradually in a direction extending axially away from said tubular catheter portion.

19. A sealed sterile intravenous catheter and needle assembly as recited in claim 17, wherein said sealed catheter assembly and said gel cap portion are configured as a one-piece unitary body.

20. A sealed sterile intravenous catheter and needle assembly as recited in claim 17, wherein said sealed catheter assembly is configured to be easily adapted for a needle-less connection.

* * * * *